(12) United States Patent
Saravanan et al.

(10) Patent No.: US 11,274,257 B2
(45) Date of Patent: Mar. 15, 2022

(54) PROCESS FOR SELECTIVE PRODUCTION OF LIGHT OLEFINS AND AROMATIC FROM CRACKED LIGHT NAPHTHA

(71) Applicant: Indian Oil Corporation Limited, Mumbai (IN)

(72) Inventors: Subramani Saravanan, Haryana (IN); Bandaru Venkata Hari Prasadgupta, Haryana (IN); Prosenjit Maji, Haryana (IN); Shoeb Hussain Khan, Haryana (IN); Jagdev Kumar Dixit, Haryana (IN); Shakti Singh, Haryana (IN); Reshmi Manna, Haryana (IN); Madhusudan Sau, Haryana (IN); Debasis Bhattacharyya, Haryana (IN); Sanjiv Kumar Mazumdar, Haryana (IN); Sankara Sri Venkata Ramakumar, Haryana (IN)

(73) Assignee: Indian Oil Corporation Limited, Mumbai (IN)

( * ) Notice: Subject to any disclaimer, the term of this patent is extended or adjusted under 35 U.S.C. 154(b) by 0 days.

(21) Appl. No.: 16/560,531

(22) Filed: Sep. 4, 2019

(65) Prior Publication Data

US 2020/0080006 A1 Mar. 12, 2020

(30) Foreign Application Priority Data

Sep. 6, 2018 (IN) .............................. 201821033531

(51) Int. Cl.
*C10G 11/05* (2006.01)
*C07C 4/06* (2006.01)
(Continued)

(52) U.S. Cl.
CPC ............. *C10G 11/05* (2013.01); *B01J 8/0278* (2013.01); *B01J 8/1827* (2013.01); *B01J 8/1881* (2013.01); *B01J 8/26* (2013.01); *C07C 4/06* (2013.01); *B01J 2208/00752* (2013.01); *B01J 2208/00761* (2013.01); *B01J 2208/00946* (2013.01);
(Continued)

(58) Field of Classification Search
None
See application file for complete search history.

(56) References Cited

U.S. PATENT DOCUMENTS 4,918,256 A * 4/1990 Nemet-Mavrodin ....................... C10G 35/095
502/77
5,026,936 A 6/1991 Leyshon et al.
(Continued)

FOREIGN PATENT DOCUMENTS

EP 0109059 A1 5/1984

*Primary Examiner* — Philip Y Louie
(74) *Attorney, Agent, or Firm* — Blank Rome LLP

(57) ABSTRACT

The present invention provides a process for a production of light olefins and aromatics from cracked light naphtha by selective cracking. The present invention thus provides a process for up grading cracked olefinic naphtha to high value petrochemical feed stocks. This process is based on catalytic cracking in which the catalyst activity is optimized by depositing coke for production of light olefins and aromatics. The proposed process has high flexibility and can be operated either in maximizing olefins as reflected from the PIE ratio or in maximizing aromatics (BTX) at different modes of operation depending upon the product requirement.

7 Claims, 2 Drawing Sheets

(51) Int. Cl.
*B01J 8/02* (2006.01)
*B01J 8/18* (2006.01)
*B01J 8/26* (2006.01)

(52) U.S. Cl.
CPC ...... *C07C 2529/08* (2013.01); *C07C 2529/40* (2013.01); *C10G 2300/1044* (2013.01); *C10G 2300/208* (2013.01); *C10G 2300/30* (2013.01); *C10G 2300/301* (2013.01); *C10G 2300/308* (2013.01); *C10G 2300/70* (2013.01); *C10G 2300/708* (2013.01); *C10G 2400/02* (2013.01); *C10G 2400/20* (2013.01); *C10G 2400/30* (2013.01)

(56) References Cited

U.S. PATENT DOCUMENTS

| | | |
|---|---|---|
| 5,160,424 A | 11/1992 | Le et al. |
| 6,069,287 A | 5/2000 | Ladwig et al. |
| 6,548,725 B2 | 4/2003 | Froment et al. |
| 6,602,403 B1 | 8/2003 | Steffens et al. |
| 7,686,942 B2 | 3/2010 | Xie et al. |
| 2001/0053868 A1* | 12/2001 | Chester ................ C10G 35/095 585/648 |
| 2005/0070422 A1 | 3/2005 | Chen et al. |

* cited by examiner

PROCESS FOR SELECTIVE PRODUCTION OF LIGHT OLEFINS AND AROMATIC FROM CRACKED LIGHT NAPHTHA

RELATED APPLICATION

This application claims the benefit of Indian Application No. 201821033531, filed on Sep. 6, 2018. The entire content of this application is incorporated herein by reference.

FIELD OF THE INVENTION

The present invention relates to a process for the production of light olefins and aromatics from cracked light naphtha by selective cracking. More specifically, the proposed process has high flexibility and can be operated either in maximizing olefins or in maximizing aromatics (benzene, toluene and xylene (BTX)) using different modes of operation depending upon the product requirement.

BACKGROUND OF THE INVENTION

Naphtha cracking is a known process for production of light olefins. Conventional steam cracking of naphtha is a thermal cracking process in which naphtha is cracked at very high temperatures in the range of 800-900° C. in presence of steam. The major products are ethylene and propylene. However, there is no control on selectivity to particular light olefins especially propylene. On the other hand, fluid catalytic cracking process can be employed for cracking naphtha to selectively produce propylene, but due to low coke yield, maintaining the heat balance is very difficult.

EP 0109 059 B1 discloses a process for catalytic cracking of olefinic hydrocarbon stream (C4-C12) over ZSM-5/11 to produce propylene along with oligomerization step. U.S. Pat. No. 5,026,936 disclose an improved method for production of propylene from C4 stream or a stream containing higher hydrocarbons. The ethylene from the reaction mixture is metathesized with C4+ olefins to form further propylene.

U.S. Pat. No. 6,548,725 B2 described an improved catalytic cracking of naphtha (C3-C12) over a pentasil zeolite catalyst in fixed/fluidized bed reactor which provides higher propylene yield with lower methane yield. The feed is sent to the reactor along with diluents of fixed molar ratio. Also they, have used propane as co-feed.

U.S. Pat. No. 6,069,287 discloses a process for selectively producing C2-C4 olefins from a catalytically, cracked or thermally cracked naphtha stream. The naphtha stream is contacted with a catalyst containing from about 10 to 50 wt. % of a crystalline zeolite. Further, an effective amount of single ring aromatics is fed to the reaction zone to also improve the selectivity of propylene vs ethylene.

US 2005/007042.2 A1 discloses a multi component catalyst and catalytic cracking process for selectively producing C3 olefins. The process is carried out by contacting a feedstock containing hydrocarbons having at least 5 carbon atoms, under catalytic cracking conditions, with the multi component catalyst.

U.S. Pat. No. 5,160,424 discloses a method for upgrading paraffinic naphtha to high octane fuel under low pressure selective cracking conditions effective to produce C4-C5 isoalkenes and C4-05 isoalkanes. The isoalkane products of cracking are dehydrogenated and etherified to provide high octane fuel components.

U.S. Pat. No. 7,686,942 B1 describes a catalyst system comprising of silica/alumina, molecular sieve (ZSM-5, SAPO, MCM) for carrying out naphtha cracking at low temperature and claims better selectivity and activity towards ethylene and propylene.

U.S. Pat. No. 6,602,403 B1 discloses a process for catalytic naphtha cracking to yield naphtha having increased concentration of iso-paraffins and less C5+ olefins i.e. low RVP and high octane.

In the petroleum refining and petrochemical industry, lot of olefinic naphtha streams are generated through various thermal and catalytic cracking processes such as delayed coking, steam cracking, fluid catalytic cracking, visbreaking etc. Most of these low value naphtha streams are routed for production of hydrogen in hydrogen generation units or to treatment unit like DHDS, DHDT etc for removal of impurities. Thus, it is necessitated to provide a process whereby the cracked low value naphtha streams gets converted to valuable light olefins and aromatics using a suitable catalyst.

SUMMARY OF THE INVENTION

Accordingly, in the present invention, cracked low value naphtha streams are selectively, converted to light olefins and aromatics using a zeolite based catalyst, preferably a pentasil type zeolite either alone or in combination of a Y-type zeolite. In the present invention, the catalyst is subjected to coke deposition and it is observed that at different coke levels on catalyst, the product yields, property and selectivity changes significantly. The catalyst contact time is higher in the process as compared to fluid catalytic cracking process, which is further optimized for producing the desired product.

The present invention relates to a process for the production of light olefins and aromatics from cracked light naphtha by selective cracking and can be operated either in maximizing olefins or in maximizing aromatics (BTX) at different modes of operation depending upon the product requirement. Further, the present invention relates to a process scheme in which a moving bed reactor is employed as a cracking reactor unlike the conventional catalytic naphtha cracking process which utilizes riser regenerator configuration. The process of present invention produces light olefins having better propylene to ethylene ratio (P/E) of 1-5. In conventional steam cracking process, this ratio is generally less than 1. The aromatic production is maximized by the addition of hydrogen in the feed stream.

The present invention provides a process for selective production of light olefins and aromatics from naphtha feedstock, the process comprising:
a) feeding a mixed olefinic cracked naphtha feedstock into a reactor;
b) catalytic cracking of the mixed olefinic cracked naphtha in the reactor under olefinic mode or aromatic mode of operation,
  (i) wherein under olefinic mode of operation, the mixed olefinic cracked naphtha is catalytically cracked by contacting with a zeolite catalyst for a residence time ranging between 35-65 minutes and at a pressure ranging between 1-2 bar to obtain cracked product comprising light olefins in the range of 30-50 wt % and obtaining the light olefins as a gaseous product with a propylene to ethylene ratio (P/E) in the range of 1-5;
  (ii) wherein under aromatic mode of operation, the mixed olefinic cracked naphtha is catalytically cracked by contacting with a zeolite catalyst for a residence time ranging between 20-35 minutes and at a pressure ranging between 5-7 bar to obtain a cracked product comprising aromatics in the range of 10-25 wt % and obtaining the aromatics as a liquid product;

c) recovering a spent catalyst from the reactor and feeding the spent catalyst to a regenerator to obtain a regenerated catalyst and recycling the regenerated catalyst to the reactor.

In one feature; the present invention further provides a system for selective production of light olefins and aromatics, wherein the system comprises;

(a) a dual functional reactor as reactor/regenerator operating in reactor mode to receive the mixed olefinic cracked naphtha feedstock,
  (i) wherein the reactor is configured for olefinic mode of operation and is operated in a fixed fluidized bed mode for a residence time ranging between 35-65 minutes and at a pressure ranging between 1-2 bar for selectively converting mixed olefinic cracked naphtha feedstock into light olefins in the range of 30-50 wt %;
  (ii) wherein the reactor is configured for aromatic mode of operation and is operated in a fixed bed mode for a residence time ranging between 20-35 minutes and at a pressure ranging between 5-7 bar for selectively converting mixed olefinic cracked naphtha feedstock into aromatics in the range of 10-25% in the liquid product;
(b) another dual functional reactor as reactor/regenerator operating in regenerator mode for burning catalyst coke in presence of air or any oxygen containing gas; wherein the dual functional reactors/regenerators are operated in swing operation mode.

Objectives of the Present Invention

The primary objective of the present invention is to provide a process for up grading cracked olefinic naphtha to high value petrochemical feed stocks by selective cracking.

Another objective of the present invention is to provide a process wherein cracked low value naphtha streams are selectively converted to light olefins and aromatics using a zeolite based catalyst, preferably a pentasil type zeolite either alone or in combination with a Y-type zeolite.

Yet another objective of the present invention is to provide a process in which a moving bed reactor is employed as a cracking reactor unlike the conventional catalytic naphtha cracking process which utilizes riser regenerator configuration.

DETAILED DESCRIPTION OF THE INVENTION

The present invention relates to a process for the production of light olefins and aromatics from cracked light naphtha by selective cracking. More specifically, the proposed process has high flexibility and can be operated either in maximizing olefins or in maximizing aromatics (BTX) at different modes of operation depending upon the product requirement. In the present invention, mixed olefinic cracked naphtha boiling in the range of C5-220° C. which is generated from various secondary processing units in a refinery such as FCCU (Fluid catalytic cracking unit), Visbreaker, Delayed coker is further catalytically cracked in a reactor. The cracked product comprises light olefins such as ethylene, propylene and butylenes and the liquid product rich in aromatics. Ethylene and propylene are recovered from the gaseous products as petrochemical feedstock. The liquid product obtained in this process is having higher octane number than that of feed as it is rich in aromatics and have lower sulfur content than that of feed. The liquid product can be directly blended into the gasoline pool or the aromatics in liquid product can be recovered in a separate recovery unit.

According to the main feature, the present invention provides a process for selective production of light olefins and aromatics from naphtha feedstock, the process comprising:

a) feeding a mixed olefinic cracked naphtha feedstock into a reactor;

b) catalytic cracking of the mixed olefinic cracked naphtha in the reactor under olefinic mode or aromatic mode of operation,
  (i) wherein under olefinic mode of operation, the mixed olefinic cracked naphtha is catalytically cracked by contacting with a zeolite catalyst for a residence time ranging between 35-65 minutes and at a pressure ranging between 1-2 bar to obtain a cracked product comprising light olefins in the range of 30-50 wt % and obtaining the light olefins as a gaseous product with a propylene to ethylene ratio (P/E) in the range of 1-5;
  (ii) wherein under aromatic mode of operation, the mixed olefinic cracked naphtha is catalytically cracked by contacting with a zeolite catalyst for a residence time ranging between 20-35 minutes and at a pressure ranging between 5-7 bar to obtain a cracked product comprising aromatics in the range of 10-25 wt % in the liquid product and obtaining the aromatics as a liquid product;

c) recovering a spent catalyst from the reactor and feeding the spent catalyst to a regenerator to obtain a regenerated catalyst and recycling the regenerated catalyst to the reactor.

Figure 1:
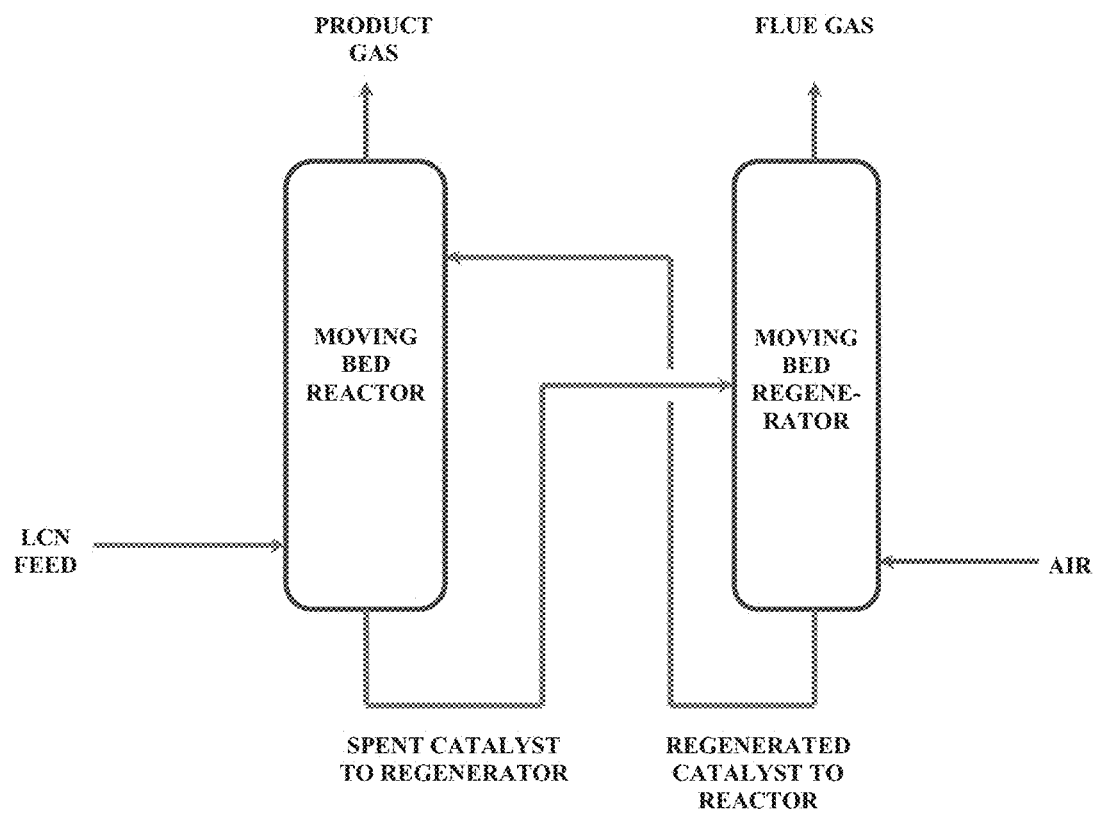
FIG. 1: Schematic representation of the process of selective catalytic cracking of mixed olefinic cracked naphtha

In a preferred feature of the present invention, the process for selective production of light olefins and aromatics from mixed olefinic cracked naphtha feedstock is schematically represented in FIG. 1. The product gas from the reactor is routed to a fractionator column followed by a Gascon section where Dry Gas, LPG and gasoline are separated. Subsequently, the light olefins are separated out as the gaseous stream and the aromatics as the heavier liquid product.

In one feature of the present invention, the mixed olefinic cracked naphtha is in the range of C5-220° C. More specifically, mixed olefinic cracked naphtha refers to a mixture containing a large number of hydrocarbon components of different groups viz. paraffins, iso-paraffins, olefins, naphthenes, aromatics and others.

In one feature of the present invention, the mixed olefinic cracked naphtha comprises 4.8 wt % of paraffins, 35.3 wt % of iso-paraffins, 39.6 wt % of olefins, 10.7 wt % of naphthenes, 8.8 wt % of aromatics and 0.8 wt % of other constituents.

In another feature of the present invention, the reactor is moving bed reactor.

In another feature of the present invention, the catalytic cracking in the process step (b) is carried out at a space velocity ranging between 10-20 hr$^{-1}$ and at a temperature of 600° C.

In yet another feature of the present invention, the aromatics comprise of BTX; wherein BTX is a combination of benzene, toluene and xylene.

In a preferred feature, in the olefinic mode of operation, the light olefin selectivity is in the range of 30-50 wt % at a coke deposition level ranging from 6 to 8 wt %. In the olefinic mode of operation, the liquid product can directly be blended to the gasoline pool without any further processing.

In yet another preferred feature, in the aromatic mode of operation, the selectivity for aromatics is in the range of 10-25 wt % and BTX concentration in the aromatics is in the range of 5-13 wt % on addition of hydrogen with the mixed olefinic cracked naphtha feedstock.

In another feature, in the aromatic mode of operation, the liquid product containing the aromatics as obtained from the catalytic cracking is blended directly into gasoline pool to obtain product gasoline. Thus, the increase in reactor pressure in the range of 5-7 bar in the aromatic mode of operation, increases the gasoline yield up to 80 wt %. Subsequently, the Research Octane Number (RON) of the product gasoline increases drastically from 82.1 to 90.4 as compared to that of feed.

In another feature of the present invention, a moving bed reactor along with a moving bed regenerator is employed in the process. The catalyst residence time in the moving bed reactor is higher (20-65 minutes) as compared to typical circulating fluid bed reactor-regenerator configuration. Further, depending on the product requirement, either catalyst residence time or the coke deposition level on the catalyst is required to be optimized.

In another feature of the present invention, the zeolite catalyst is a pentasil type zeolite used either alone or in combination with a Y-type zeolite. The pentasil type zeolite is ZSM-5, and the Y-type zeolite is selected from the group consisting of Zeolite-Y (Na—Y), USY and Rare earth exchanged-Y.

Figure 2:
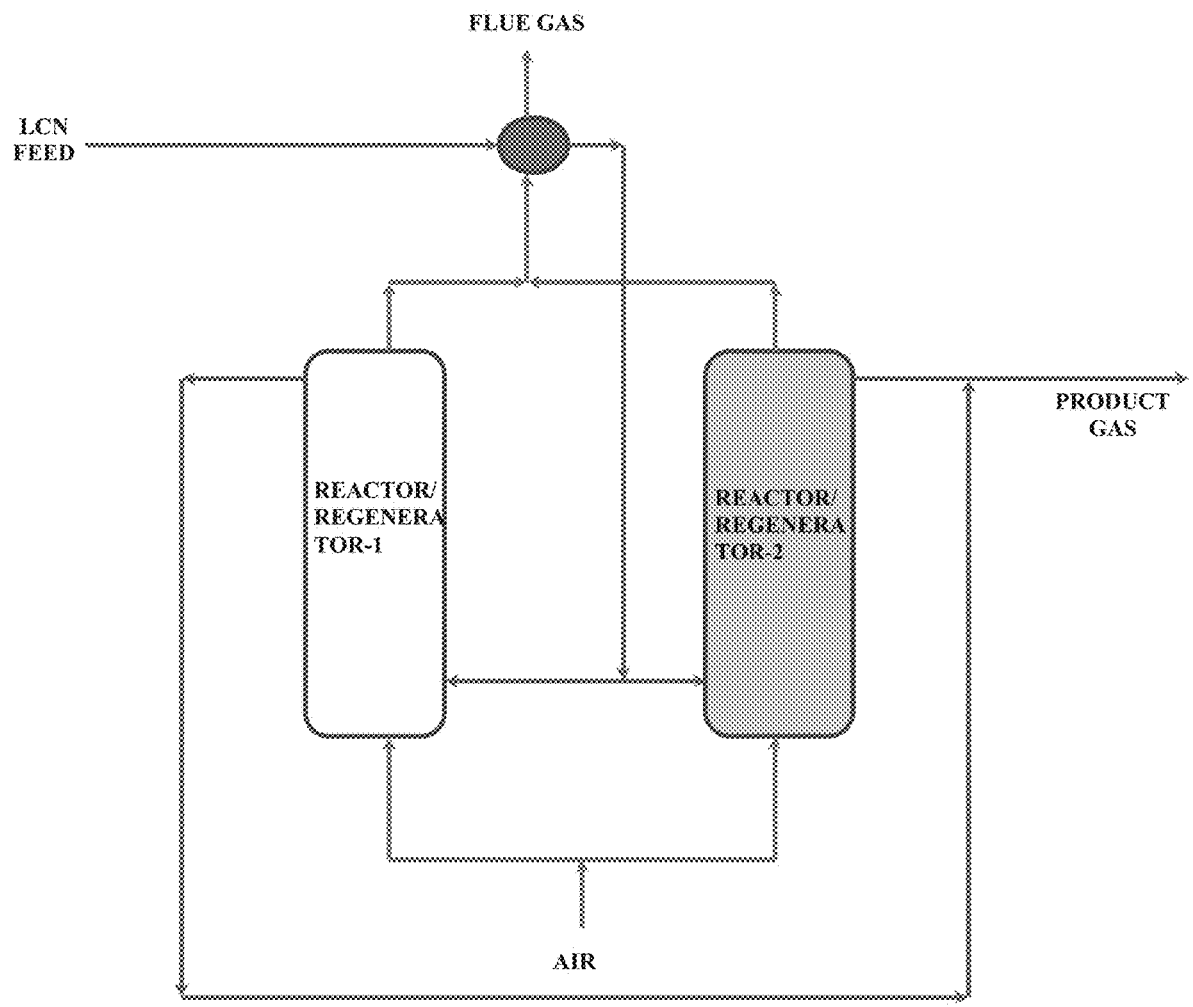
FIG. 2: Dual functional reactor as reactor/Regenerator

In a preferred feature of the present invention, FIG. 2 shows the schematic representation of a dual functional reactor/regenerator operation in swing operation mode. Light cracked naphtha (LCN) feed enters the Reactor-1 after exchanging the heat with the flue gas from Regenerator-2. The reactor is operated in fixed fluidized bed mode or in a fixed bed mode and the feed is passed inside the reactor as per the conditions for the olefinic mode or aromatics mode of operation depending upon the product requirement. After completion of the reaction time, the reactor catalyst is stripped with steam to remove entrapped hydrocarbons and switched to regenerator mode for burning the catalyst coke in presence of air or any oxygen containing gas. During the regeneration mode of Reactor-1, Reactor-2 will be operated in reactor mode. This can be operated in swing mode of operation by employing n-number of reactor/regenerator train, which depends upon the feed throughput and quality. The product gas from the reactor is routed to a fractionator column for separation of the light olefins as the gaseous product and the aromatics as the heavier liquid product.

In yet another feature, the present invention provides a system for selective production of light olefins and aromatics, wherein the system comprises;
(a) a dual functional reactor as reactor/regenerator operating in reactor mode to receive the mixed olefinic cracked naphtha feedstock,
 (i) wherein the reactor is configured for olefinic mode of operation and is operated in a fixed fluidized bed mode for a residence time ranging between 35-65 minutes and at a pressure ranging between 1-2 bar for selectively converting mixed olefinic cracked naphtha feedstock into light olefins in the range of 30-50 wt %;
 (ii) wherein the reactor is configured for aromatic mode of operation and is operated in a fixed bed mode for a residence time ranging between 20-35 minutes and at a pressure ranging between 5-7 bar for selectively converting mixed olefinic cracked naphtha feedstock into aromatics in the range of 10-25 wt % in the liquid product;
(b) another dual functional reactor as reactor/regenerator operating in regenerator mode for burning catalyst coke in presence of air or any oxygen containing gas;
wherein the dual functional reactors/regenerators are operated in swing operation mode.

The following are the advantages of the present invention:

Production of light olefins (C2= and C3=) having higher PIE ratio.

Flexibility of operating the unit at different modes with respect to desired product yield.

Operated in either maximizing light olefin yield or maximizing aromatics yield.

The following examples are given for the purpose of further illustrating the invention. All percentages and parts are based on weight unless otherwise indicated.

Experiments are conducted in a micro reactor at various pressures, temperatures and space velocities using an olefinic cracked naphtha stream generated from a FCC unit. The properties of feed used for these experiments are indicated in Table-1.

TABLE 1

| Properties of feed | |
|---|---|
| Density, gm/cc | 0.7009 |
| Distillation, D-2887, wt % | |
| 5% | 25.1 |
| 10% | 28.4 |
| 30% | 49.8 |
| 50% | 75.5 |
| 70% | 99.0 |
| 90% | 133.9 |
| 95% | 143.0 |

Example-1

Using the above feedstock as indicated in Table 1, experiments are conducted at various pressures and at different residence time to identify the pressure required for conducting the reaction and the yield obtained at different residence times. The details of the experiments are indicated in Table 2.

TABLE 2

Effect of pressure and time on stream (residence time)

| Process parameters | Present Invention | | | | | | | |
|---|---|---|---|---|---|---|---|---|
| Reaction pressure, bar | 1 | | | | | 5 | | |
| Feed rate, gm/min | 0.7 | | | | | 0.7 | | |
| Catalyst loaded, gm | 2.0 | | | | | 2.0 | | |
| Time on stream, min | 5 | 20 | 35 | 50 | 65 | 5 | 20 | 35 |
| Reaction temperature, °C. | 600 | 600 | 600 | 600 | 600 | 600 | 600 | 600 |
| Product yields, wt % | | | | | | | | |
| Dry gas | 16.46 | 16.61 | 9.74 | 10.67 | 9.51 | 15.48 | 16.48 | 14.18 |
| LPG | 34.12 | 44.77 | 31.75 | 38.29 | 38.54 | 24.26 | 21.95 | 16.97 |
| Gasoline | 48.53 | 37.96 | 58.07 | 50.49 | 51.49 | 59.25 | 60.64 | 68.10 |
| P/E ratio (wt/wt) | 1.35 | 2.18 | 2.86 | 3.50 | 4.07 | 1.02 | 1.10 | 1.36 |
| BTX in product gasoline, wt % | 2.74 | 2.34 | 3.58 | 1.18 | 1.20 | 4.45 | 5.05 | 5.75 |

| Process parameters | Present Invention | | | | | | |
|---|---|---|---|---|---|---|---|
| Reaction pressure, bar | 5 | | 7 | | | | |
| Feed rate, gm/min | 0.7 | | 0.7 | | | | |
| Catalyst loaded, gm | 2.0 | | 2.0 | | | | |
| Time on stream, min | 50 | 65 | 5 | 20 | 35 | 50 | 65 |
| Reaction temperature, °C. | 600 | 600 | 600 | 600 | 600 | 600 | 600 |
| Product yields, wt % | | | | | | | |
| Dry gas | 14.12 | 15.18 | 6.92 | 9.61 | 8.05 | 11.03 | 10.34 |
| LPG | 16.67 | 17.30 | 13.49 | 17.87 | 13.58 | 17.23 | 16.87 |
| Gasoline | 68.40 | 66.72 | 79.41 | 72.34 | 78.23 | 71.58 | 72.65 |
| P/E ratio (wt/wt) | 1.59 | 1.70 | 1.17 | 1.21 | 1.22 | 1.23 | 1.33 |
| BTX in product gasoline, wt % | 3.48 | 3.40 | 3.85 | 5.9 | 5.55 | 3.65 | 3.9 |

From Table 2, it is observed that low pressure favors the olefins production, whereas at high pressure gasoline yield as well as BTX yield in product gasoline is maximized. Further, the trend of increase in light olefins yield with time on stream is similar in both the cases, which in turn indicates the effect of coke deposition level on the selectivity of propylene.

Example-2

In order to identify the required space velocity for the two modes of operation as explained in the above sections, experiments are conducted at constant temperature of 600° C. and at a pressure of 1 bar using the feed as described in Table 1 at various space velocities. The details of the experiments are indicated in Table 3.

be optimum. Further, it is also evident that at a constant temperature, pressure and space velocity, the yield of propylene is dependent on the time on stream. Therefore, the extent of coke deposition on the catalyst particle modifies the catalyst behavior which is responsible for the increase in propylene selectivity. The coke level on the catalyst collected after 50-65 minutes of operation is found to be in the range of 6-8 wt %, hence this level will be maintained in the moving bed reactor to obtain the higher P/E ratio.

Example-3

In order to identify the required space velocity for the two modes of operation as explained in the above sections, experiments were conducted at constant temperature of 600° C. and at a pressure of 5 bar using the feed as described in Table 1 at various space velocities. The details of the experiments are indicated in Table 4.

TABLE 3

Effect of space velocity at a pressure of 1 bar

| Reaction pressure, bar | 1 | | | | | | | | | |
|---|---|---|---|---|---|---|---|---|---|---|
| Reaction temperature, °C. | 600 | | | | | | | | | |
| Time on stream, min | 5 | 20 | 35 | 50 | 65 | 5 | 20 | 35 | 50 | 65 |
| Feed rate, gm/min | 0.70 | 0.70 | 0.70 | 0.70 | 0.70 | 0.35 | 0.35 | 0.35 | 0.35 | 0.35 |
| Catalyst loaded, gm | 2.0 | 2.0 | 2.0 | 2.0 | 2.0 | 2.0 | 2.0 | 2.0 | 2.0 | 2.0 |
| Space velocity, h$^{-1}$ | 20 | 20 | 20 | 20 | 20 | 10 | 10 | 10 | 10 | 10 |
| Product yields, wt % | | | | | | | | | | |
| Dry gas | 16.46 | 16.61 | 9.74 | 10.67 | 9.51 | 39.26 | 29.57 | 27.55 | 27.66 | 25.44 |
| LPG | 34.12 | 44.77 | 31.75 | 38.29 | 38.54 | 38.10 | 53.45 | 55.28 | 53.77 | 53.69 |
| Gasoline | 48.53 | 37.96 | 58.07 | 50.49 | 51.49 | 20.86 | 15.77 | 16.30 | 17.41 | 19.97 |
| P/E ratio (wt/wt) | 1.35 | 2.18 | 2.86 | 3.50 | 4.07 | 0.84 | 1.30 | 1.6 | 1.71 | 1.55 |
| BTX in product gasoline, wt % | 2.74 | 2.34 | 3.58 | 1.18 | 1.20 | 0.60 | 2.70 | 2.79 | 3.20 | 3.68 |

From Table 3, it is observed that for maximum production of propylene, low severity (high space velocity) is found to

TABLE 4

Effect of space velocity at a pressure of 5 bar

| | | | | | | | | | | |
|---|---|---|---|---|---|---|---|---|---|---|
| Reaction pressure, bar | | | | | 5 | | | | | |
| Reaction temperature, °C. | | | | | 600 | | | | | |
| Time on stream, min | 5 | 20 | 35 | 50 | 65 | 5 | 20 | 35 | 50 | 65 |
| Feed rate, gm/min | 0.70 | 0.70 | 0.70 | 0.70 | 0.70 | 0.35 | 0.35 | 0.35 | 0.35 | 0.35 |
| Catalyst loaded, gm | 2.0 | 2.0 | 2.0 | 2.0 | 2.0 | 2.0 | 2.0 | 2.0 | 2.0 | 2.0 |
| Space velocity, $h^{-1}$ | 20 | 20 | 20 | 20 | 20 | 10 | 10 | 1.0 | 10 | 10 |
| Product yields, wt % | | | | | | | | | | |
| Dry gas | 15.48 | 16.48 | 14.18 | 14.12 | 15.18 | 16.02 | 16.03 | 16.59 | 16.75 | 16.40 |
| LPG | 24.26 | 21.95 | 16.97 | 16.67 | 17.30 | 28.29 | 25.81 | 25.27 | 24.34 | 23.17 |
| Gasoline | 59.25 | 60.64 | 68.10 | 68.40 | 66.72 | 55.38 | 57.88 | 57.89 | 58.67 | 60.23 |
| P/E ratio (wt/wt) | 1.02 | 1.10 | 1.36 | 1.59 | 1.70 | 1.44 | 1.47 | 1.52 | 1.56 | 1.66 |
| BTX in product gasoline, wt % | 4.45 | 5.05 | 5.75 | 3.48 | 3.40 | 5.39 | 6.23 | 4.09 | 3.96 | 3.56 |

From Table 4, it is observed that for maximum concentration of BTX in product gasoline, high severity (low space velocity) is found to be optimum. Further, it is also evident that at a constant temperature, pressure and space velocity, the concentration of BTX is dependent on the time on stream. Maximum concentration of BTX is achieved at a time on stream value of 20 minutes. Therefore, the extent of coke deposition on the catalyst particle modifies the catalyst behavior which is responsible for the lowering of selectivity for production of aromatics at higher residence time.

Example-4

The experiments as described in the above examples were conducted in nitrogen atmosphere. In order to understand the effect of hydrogen addition on the propylene yield and BTX yield in product gasoline, experiments were conducted at 1 bar pressure in hydrogen environment using the feed stock as indicated in Table 1. The details of the experiments are indicated in Table 5.

TABLE 5

Effect of hydrogen at a pressure of 1 bar

| | 1 bar $N_2$ pressure | | | | | 1 bar $H_2$ pressure | | | | |
|---|---|---|---|---|---|---|---|---|---|---|
| Reaction pressure, bar | | | | | | | | | | |
| Reaction temperature, °C. | 600 | | | | | 600 | | | | |
| Time on stream, min | 5 | 20 | 35 | 50 | 65 | 5 | 20 | 35 | 50 | 65 |
| Feed rate, gm/min | 0.70 | 0.70 | 0.70 | 0.70 | 0.70 | 0.70 | 0.70 | 0.70 | 0.70 | 0.70 |
| Catalyst loaded, gm | 2.0 | 2.0 | 2.0 | 2.0 | 2.0 | 2.0 | 2.0 | 2.0 | 2.0 | 2.0 |
| Space velocity, $h^{-1}$ | 20 | 20 | 20 | 20 | 20 | 20 | 20 | 20 | 20 | 20 |
| Product yields, wt % | | | | | | | | | | |
| Dry gas | 16.46 | 16.61 | 9.74 | 10.67 | 9.51 | 13.07 | 12.63 | 9.89 | 9.89 | 13.07 |
| LPG | 34.12 | 44.77 | 31.75 | 38.29 | 38.54 | 27.94 | 31.78 | 31.81 | 31.81 | 27.94 |
| Gasoline | 48.53 | 37.96 | 58.07 | 50.49 | 51.49 | 57.70 | 54.42 | 57.13 | 57.13 | 57.70 |
| P/E ratio (wt/wt) | 1.35 | 2.18 | 2.86 | 3.50 | 4.07 | 1.27 | 1.87 | 2.83 | 2.83 | 1.27 |
| BTX in product gasoline, wt % | 2.74 | 2.34 | 3.58 | 1.18 | 1.20 | 2.69 | 2.78 | 3.12 | 4.20 | 2.26 |

It is observed from Table 5 that the addition of hydrogen with feed at a pressure of 1 bar does not result in an improvement in the yield of propylene. Maximum P/E ratio is obtained at a time on stream value of 65 minutes under 1 bar $N_2$ pressure. The results indicate that an optimum coke deposition favours the production of light olefins. It is further observed that at a pressure of 1 bar neither of the gases exerts any significant effect on the production of BTX.

Example-5

The experiments as described in the above examples 1-3 were conducted in nitrogen atmosphere. Further, experiments were conducted at 5 bar pressure in both hydrogen and nitrogen environments using the feed stock as indicated in Table 1, in order to understand the effect of hydrogen and nitrogen addition on the propylene yield and BTX yield in product gasoline at the desired pressure. The details of the experiments are indicated in Table 6.

TABLE 6

Effect of hydrogen at a pressure of 5 bar

| Reaction pressure, bar | 5 bar N$_2$ pressure | | | | | 5 bar H$_2$ pressure | | | | |
|---|---|---|---|---|---|---|---|---|---|---|
| Time on stream, min | 5 | 20 | 35 | 50 | 65 | 5 | 20 | 35 | 50 | 65 |
| Feed rate, gm/min | 0.70 | 0.70 | 0.70 | 0.70 | 0.70 | 0.70 | 0.70 | 0.70 | 0.70 | 0.70 |
| Catalyst loaded, gm | 2.0 | 2.0 | 2.0 | 2.0 | 2.0 | 2.0 | 2.0 | 2.0 | 2.0 | 2.0 |
| Reaction temperature, ° C. | 600 | 600 | 600 | 600 | 600 | 600 | 600 | 600 | 600 | 600 |
| Space velocity, h$^{-1}$ | 20 | 20 | 20 | 20 | 20 | 20 | 20 | 20 | 20 | 20 |
| Product yields, wt % | | | | | | | | | | |
| Dry gas | 15.48 | 16.48 | 14.18 | 14.12 | 15.18 | 11.77 | 13.21 | 11.15 | 12.07 | 12.35 |
| LPG | 24.26 | 21.95 | 16.97 | 16.67 | 17.30 | 13.59 | 19.09 | 16.17 | 14.58 | 15.90 |
| Gasoline | 59.25 | 60.64 | 68.10 | 68.40 | 66.72 | 73.17 | 66.17 | 71.37 | 71.74 | 70.63 |
| P/E ratio (wt/wt) | 1.02 | 1.10 | 1.36 | 1.59 | 1.70 | 0.72 | 1.09 | 1.37 | 1.43 | 1.53 |
| BTX in product gasoline, wt % | 4.45 | 5.05 | 5.75 | 3.48 | 3.40 | 2.70 | 12.48 | 5.98 | 3.57 | 3.23 |

It is observed from Table 6 that the addition of hydrogen with feed at a pressure of 5 bar not only increases the gasoline yield but also increases aromatics concentration. It is also seen that the aromatics production is maximum at time on stream of 20 minutes and then reduces. This indicates that the optimum coke level is required to be maintained for maximizing aromatics content in the liquid gasoline product. Further, it is also seen that hydrogen addition has no significant role on P/E ratio at a pressure of 5 bar.

Example-6

The examples from 1-5 describe the impact of various operating conditions such as pressure, space velocity, time on stream on light olefins yield as well as on BTX concentration in the product gasoline. This example shows the effect on product properties such as RON and sulfur content.

TABLE 7

Liquid product properties

| Feed RON | 82.1 | 82.1 |
|---|---|---|
| Feed sulfur, ppmw | 185 | 185 |
| Feed rate, gm/min | 0.70 | 0.35 |
| Catalyst loaded, gm | 2.0 | 2.0 |
| Reaction pressure, bar | 1 | 1 |
| Reaction temperature, ° C. | 600 | 600 |
| Time on stream, min | 50 | 50 |
| Space velocity, h$^{-1}$ | 20 | 10 |
| Product RON | 84.7 | 90.4 |
| Product sulfur, ppmw | 158 | 143.3 |

From Table 7, it is observed that there is a significant increase in RON of product gasoline as compared to feed. However, at high severity, RON increases drastically from 82.1 to 90.4.

Based on Examples 1-5, Table 8 has been summarized to indicate the selectivity of the process for the production of light olefins and aromatics under the desired conditions of the process parameters, in olefinic and aromatic modes of operation respectively.

TABLE 8

Yield of light olefins and aromatics in olefinic and aromatic modes of operation

| Modes of operation | Process parameters | Light olefin (% yield, wt %) | Aromatics in Gasoline, wt % |
|---|---|---|---|
| Olefinic | Pressure: 1 bar; TOS: 20 minutes | 36.38 | 14.02 |
| | Pressure: 1 bar; TOS: 35 minutes | 41.23 | 12.23 |
| | Pressure: 1 bar; TOS: 50 minutes | 47.31 | 11.15 |
| | Pressure: 1 bar; TOS: 65 minutes | 43.29 | 10.06 |
| Aromatic | Pressure: 5 bar; TOS: 20 minutes | 16.57 | 24.88 |
| | Pressure: 7 bar; TOS: 35 minutes | 16.13 | 23.35 |
| | Pressure: 5 bar; TOS: 50 minutes | 18.17 | 10.02 |
| | Pressure: 7 bar; TOS: 65 minutes | 19.74 | 10.46 |

Form Table 8, it is observed that in the olefinic mode of operation, the maximum selectivity for the light olefins is achieved over TOS in the range of 35-65 minutes. Again in the aromatic mode of operation, it is observed that maximum selectivity for the aromatics is shown over TOS in the range of 20-35 minutes.

The invention claimed is:

1. A process for selective production of light olefins and aromatics, the process comprising:
   a) feeding a mixed olefinic cracked naphtha feedstock into a reactor, wherein the mixed olefinic cracked naphtha feedstock is a mixture containing paraffins, iso-paraffins, olefins, naphthenes, and aromatics;
   b) catalytically cracking the mixed olefinic cracked naphtha feedstock in the reactor selectively under an olefinic mode or an aromatic mode of operation,
      (i) wherein the olefinic mode of operation comprises: contacting the mixed olefinic cracked naphtha feedstock with a zeolite catalyst for a catalyst residence time ranging between 35-65 minutes and at a pressure ranging between 1-2 bar to obtain a cracked product comprising light olefins in the range of 30-50 wt % and obtaining the light olefins as a gaseous product with a propylene to ethylene ratio (P/E) in the range of 1-5;
      (ii) wherein the aromatic mode of operation comprises: adding hydrogen to the mixed olefinic cracked naphtha feedstock to form a mixture; and contacting the mixture with a zeolite catalyst for a catalyst residence time ranging between 20-35 minutes and at a pressure ranging between 5-7 bar to obtain a cracked product comprising aromatics in the range of 10-25 wt % and obtaining the aromatics as a liquid product;

wherein the zeolite catalyst in the olefinic mode of operation and in the aromatic mode of operation consists of pentasil type zeolite used either alone or in combination with a Y-type zeolite; wherein the pentasil type zeolite is ZSM-5, and Y-type zeolite is selected from the group consisting of Zeolite-Y (Na-Y). USY and Rare earth exchanged-Y; and c) recovering spent catalyst from the reactor and feeding the spent catalyst to a regenerator to obtain a regenerated catalyst and recycling the regenerated catalyst to the reactor.

2. The process as claimed in claim 1, wherein the mixed olefinic cracked naphtha is in the range of C5-220° C.

3. The process as claimed in claim 1, wherein the catalytic cracking in step (b) is carded out at a space velocity ranging between 10-20 hr$^{-1}$ and at a temperature of 600° C.

4. The process as claimed in claim 1, wherein the aromatics comprise of BTX;
wherein BTX is a combination of benzene, toluene and xylene.

5. The process as claimed in claim 1, wherein in the olefinic mode of operation, the light olefin selectivity is in the range of 30-50 wt % at a colic deposition level ranging from 6 to 8 wt %.

6. The process as claimed in claim 1, wherein in the aromatic mode of operation, the selectivity for aromatics is in the range of 10-25 wt % in the liquid product and BTX concentration in the aromatics is in the range of 5-13 wt % on addition of hydrogen with the mixed olefinic cracked naphtha feedstock.

7. The process as claimed in claim 1, wherein the liquid product obtained in step (b) is blended directly into gasoline pool to obtain product gasoline.

* * * * *